United States Patent [19]

Fake

[11] 3,960,879

[45] *June 1, 1976

[54] NON-TOXIC ADL ANTIHYPERTENSIVES

[75] Inventor: Charles Sylvester Fake, Harlow, England

[73] Assignee: Beecham Group Limited, Brentford, England

[ * ] Notice: The portion of the term of this patent subsequent to Dec. 10, 1991, has been disclaimed.

[22] Filed: July 8, 1974

[21] Appl. No.: 486,366

[30] Foreign Application Priority Data

July 7, 1973 United Kingdom............ 32462/73

[52] U.S. Cl............................. 260/297 B; 424/263; 260/295 F
[51] Int. Cl.² ...................................... C07D 211/68
[58] Field of Search .............................. 260/297 B

[56] References Cited
UNITED STATES PATENTS

| 3,707,474 | 12/1972 | Razdan et al. ............ 260/297 B X |
| 3,853,899 | 12/1974 | Fake........................... 260/297 B |

FOREIGN PATENTS OR APPLICATIONS

| 772,492 | 3/1972 | Belgium ........................ 260/297 B |
| 1,360,009 | 7/1974 | United Kingdom............ 260/297 B |

Primary Examiner—John D. Randolph

[57] ABSTRACT

Compounds of the formula (I)

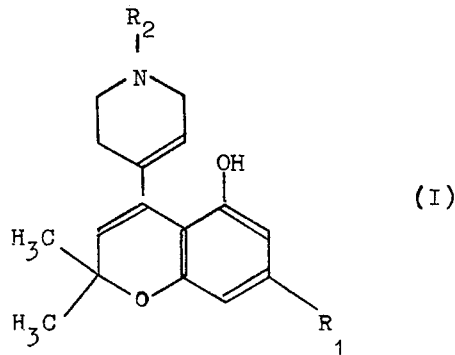

wherein $R_1$ is an alkyl group of 4 – 8 carbon atoms, $R_2$ is a naphthylmethyl group and their salts, ethers and esters have been found to possess good antihypertensive activity coupled with low toxicity. Such compounds may be prepared by the reduction of a quaternary salt of the corresponding pyridyl compound.

13 Claims, No Drawings

NON-TOXIC ADL ANTIHYPERTENSIVES

BACKGROUND TO THE INVENTION

British Pat. No. 1,360,009 disclosed inter alia certain compounds having cardiovascular and central nervous system activity. These compounds included those of the formula (II):

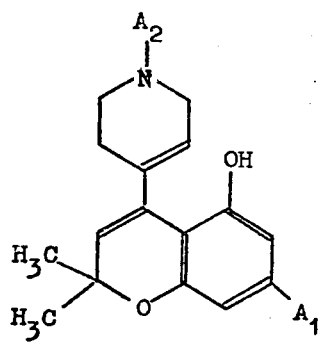

wherein $A_1$ was an aliphatic group of 1 – 20 carbon atoms, $A_2$ is an optionally substituted hydrocarbon group of 1 – 20 carbon atoms.

U.S. patent application Ser. No. 324,222, U.S. Pat. No. 3,853,899 diclosed the excellent antihypertensive activity of compounds including those of the formula (III):

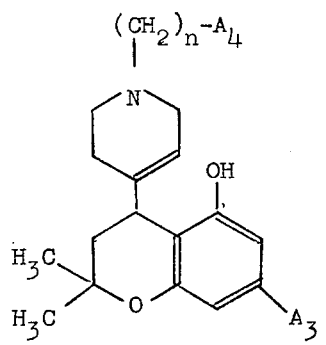

wherein $R_3$ is an alkyl group of 5 – 8 carbon atoms, $n$ is 1 or 2 and $A_4$ is a phenyl or naphthyl group.

Compounds of formulae (II) and (III) are now believed to represent classes of potentially very useful antihypertensive agents. However it has now been found that certain related compounds (of formula (I) as discussed below) have anti-hypertensive activity at least as good as the compounds of formula (II) or (III) specifically prepared in the above mentioned patent specifications and also possess the surprising advantage of a considerably improved therapeutic ratio especially with regard to renal toxicity. No certain explanation for this improvement can as yet be postulated but the advantages of the new compounds have been confirmed by repeated experimentation.

DESCRIPTION OF THE INVENTION

The present invention relates to compounds of the formula (I):

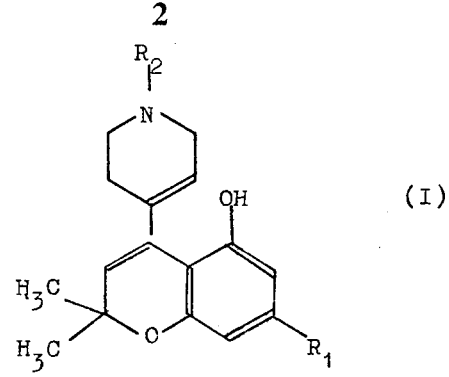

wherein $R_1$ is an alkyl group of 4 – 8 carbon atoms, $R_2$ is a naphthylmethyl group and their pharmaceutically acceptable salts, esters and ethers.

Suitable salts include acid addition salts of the basic nitrogen atom, for example, the salts formed with hydrochloric, hydrobromic, phosphoric, sulphuric, methanesulphonic, acetic, propionic, citric, lactic, tartaric, succinic, gluceronic and like acids. Other salts include sodium, potassium, magnesium or like salts.

Compound of formula (I) may be presented in a hydrated form.

Suitable ethers and esters include those wherein the phenolic hydroxyl group of the compound of formula (I) is substituted by a group —CO.$R_3$ or —$R_3$ where $R_3$ is methyl, ethyl, propyl, dimethylaminoethyl, diethylaminoethyl, dimethylaminopropyl, diethylaminopropyl, N-piperidylethyl or the like.

Suitable groups $R_1$ include the $CH(CH_3)C_4H_9$, n-$C_5H_{11}$, $C(CH_3)C_5H_{11}$, n-$C_6H_{13}$, $CH(CH_3)C_6H_{13}$, n-$C_7H_{15}$, $CH(CH_3)CH(CH_3)C_3H_7$ and like groups.

Such groups $R_1$ are preferably straight chained or carry a methyl group on the α-carbon atom, on the β-carbon atom or on both the α- and β-carbon atoms.

Preferred compounds of formula (I) include those of formula (IV):

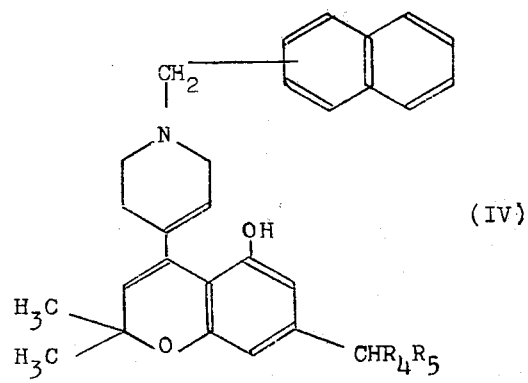

and their salts and methyl ethers or acetyl esters wherein $R_4$ is a hydrogen atom or a methyl group and $R_5$ is a n-propyl, n-butyl or n-pentyl group.

Preferably $R_5$ is a n-butyl group.

Preferably $R_4$ is a hydrogen atom.

The compounds of formula (I) (or their ethers) may be prepared by the reduction of a compound of the formula (V):

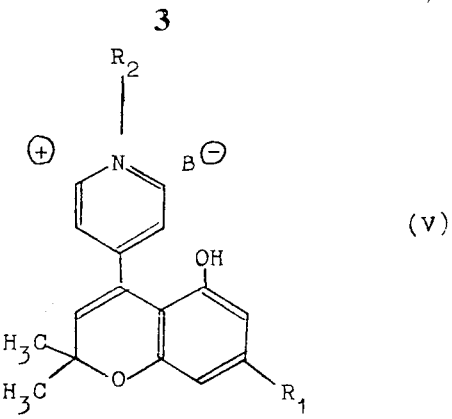

(or their ethers) wherein $R_1$ and $R_2$ are as defined in relation to formula (I) and $B^-$ is a chloride, bromide or iodide ion or the like ion.

Such reduction reactions are effected using a borohydride such as sodium borohydride under conventional conditions such as by reaction in an aqueous alcoholic solvent at ambient temperature. 3:1 mixture of ethanol or methanol with water have proven particularly good reaction media.

Esters of the compounds of formula (IV) may be prepared in conventional manner by reaction with an acid anhydride, acid halide or the like.

The compounds of formula (V) may be prepared by the reaction of a compound of the formula (VI):

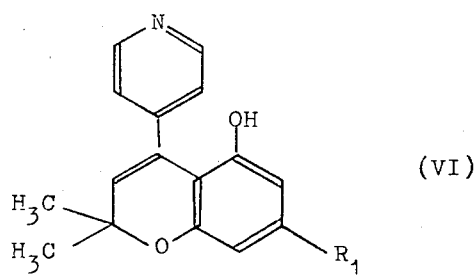

(or an ether thereof) wherein $R_1$ is as defined in relation to formula (I) with a compound of the formula (VII):

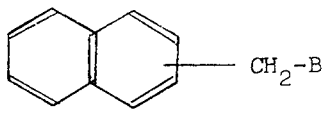

wherein B is Cl, Br, I or the like good leaving group.

The compounds of formula (I) possess useful antihypertensive activity. Accordingly in one of its aspects the present invention provides a pharmaceutical composition which comprise an anti-hypertensively effective amount of a compound of the formula (I) or a salt, ester or ether thereof, together with a pharmaceutically acceptable carrier.

The compositions of this invention can be provided as orally or parenterally administrable forms, for example, tablets, capsules, injectable forms and the like may be used.

The following examples illustrate the invention:

EXAMPLE 1

7-n-Amyl-2,2-dimethyl-4-[1-(2-naphthylmethyl)-1,2,5,6-tetrahydropyride-4-yl]-2H-chromen-5-ol 7-n-Amyl-2,2-dimethyl-4-(4-pyridyl)-2H-chromen-5-ol (5.00 g), 2-(bromomethyl)naphthalene (3.31 g) and acetone (70 ml) were heated together under reflux for 1½ hours. The mixture was then concentrated to half-volume and allowed to cool. The pale yellow crystalline solid was filtered, washed with acetone and dried under vacuum to yield 4-(7-n-amyl-5-hydroxy-2,2-dimethyl-2H-chromen-4-yl)-1-(2-naphthylmethyl) pyridinium bromide (5.70 g), p. 259°–260°.

This quaternary salt (5.34 g) was dissolved in a mixture of ethanol (250 ml) and water (75 ml). Excess sodium borohydride (approximately 1.00 g) was added portionwise over one-half hour to the stirred solution at ambient temperature and the mixture was finally stirred for a further one-half hour to ensure complete reaction.

Water (300 ml) was then added and the mixture was extracted thoroughly with ether (4 × 250 ml). The combined ether extract were washed with water, dried over anhydrous sodium sulphate, and evaporated to dryness under reduced pressure. The solid residue (4.19 g) was recrystallized from 60°–80° petroleum-ether to give the terahydopyridine (3.10 g) as colorless microcrystals mp 131°–132°.

EXAMPLE 2

7-n-Amyl-2,2-dimethyl-4-[1-(1-naphthylmethyl)-1,2,5,6-tetrahydropyrid-4-yl]-2H-chromen-5-ol 7-n-Amyl-2,2-dimethyl-4-(4-pyridyl)-2H-chromen-5-ol (5.00 g), 1-(chloromethyl) naphthalene (3.00 g), a crystal of potassium iodide and acetone (70 ml) were heated together under reflux for 1 hour. The solution was then concentrated to half-volume and allowed to stand at ambient temperature for 16 hours to yield a yellow crystalline precipitate of 4-(7-n-amyl-5-hydroxy-2,2-dimethyl-2H-chromen-4-yl)-1-(1-naphthylmethyl) pyridinium chloride (5.06 g), mp 259°–261°.

This quaternary salt (5.00 g) was dissolved in a mixture of ethanol (120 ml) and water (40 ml) and excess sodium borohydride was added portionwise to the stirred solution at ambient temperature. Work-up as described in Example 1 yielded the tetrahydropyridine (4.08 g), mp 51°–53° (crystallized with difficulty from benzene/60°–80° petroleum ether).

EXAMPLE 3

7-(2-hexyl)-2,2-dimethyl-4-[1-(2-naphthylmethyl)-1,2,5,6-tetrahydropyrid-4-yl]-2H-chromen-5-ol 7-(2-Hexyl)-2,2-dimethyl-4-(4-pyridyl)-2H-chromen-5-ol (5.00 g), 2-bromomethyl-naphthalene (3.54 g) and acetone (70 ml) were heated together under reflux for 6 hours. The resulting pale yellow precipitate was filtered and dried to yield 4-[7-(2-hexyl)-5-hydroxy-2,2-dimethyl-2H-chromen-4-yl]-1-(2-naphthylmethyl) pyridinium bromide (8.20 g) m.p. 236°–239°.

This quaternary salt (8.10 g) was dissolved in ethanol (150 ml) and water (50 ml) and excess sodium borohydride was added portionwise to the stirred solution at ambient temperature. Work-up as described in Example 1 yielded the tetrahydropyridine (4.11 g) m.p. 153°–154° (ex 60°–80° petroleum ether).

EXAMPLE 4

7-(2-Hexyl)-2,2-dimethyl-4-[1-(1-naphthylmethyl)-1,2,5,6-tetrahydropyrid-4-yl]-2H-chromen-5-ol 7-(2-Hexyl)-2,2-dimethyl-4-(4-pyridyl)-2H-chromen-5-ol (5.00 g)., 1-chloromethyl-naphthalene (2.64 g) and acetone (70 ml) were heated together under reflux for 6 hours. The resulting yellow precipitate was filtered and dried to yield 4-[7-(2-hexyl)-5-hydroxy-2,2-dimethyl-2H-chromen-4-yl]-1-(1naphthylmethyl) pyridinium chloride (5.13 g) m.p. 258°–260°.

This quaternary salt (5.13 g) was dissolved in ethanol (300 ml) and water (100 ml) and excess sodium borohydride was added portionwise to the stirred solution at ambient temperature. Work-up as described in Example 1 yield the tetrahydropyridine (2.38 g) m.p. 98°–100° (ex 60°–80° petroleum-ether).

EXAMPLE 5

5-Acetoxy-7-n-amyl-2,2-dimethyl-4-[1-(2-naphthylmethyl)1,2,5,6-tetrahydropyrid-4-yl]-2H-chromene 7-n-Amyl-2,2-dimethyl-4-[1-(2-naphthylmethyl)-1,2,5,6-tetrahydropyrid-4-yl]-2H-chromen-5-ol (1.52 g; prepared as described in Example 1), anhydrous sodium acetate (0.27 g) and acetic anhydride (10 ml) were heated together under reflux for 4 hours. The solution was then poured into ice-water (150 ml) and basified with saturated sodium bicarbonate solution. The basic solution was extracted with ether and the ethereal extracts were dried over sodium sulphate. Evaporation to dryness in vacuo gave a gum, which was purified via column chromatography on silica gel using diethyl-ether/60°–80° petroleum ether mixtures as eluent to yield the acetate (1.05 g) as a straw colored viscous oil.

EXAMPLE 6

4-Diethyl-aminobutoxy-7-(n-amyl)-4-[1-(2-naphthylmethyl)-1,2,5,6-tetrahydropyrid-4-yl]-2,2-dimethyl-2H-chromen-5-yl dihydrochloride 7-n-Amyl-2,2-dimethyl-4-[1-(2-naphthylmethyl)-1,2,5,6-tetrahydropyrid-4-yl]-2H-chromen-5-ol (4.56 g; prepared as described in Example 1), 4-diethylaminobutyric acid hydrochloride (1.96 g), dicyclohexylcarbodi-imide (2.10 g) and dichloromethane (150 ml) were stirred together for 10 days. The solution was then concentrated to 40 ml and dry ether was added. The resulting precipitate was filtered and recrystallized from ethanol-ether to yield the basic ester as a dihydrochloride (2.89 g) m.p. 126°–130°.

EXAMPLE 7

7-(n-Amyl)-5-methoxy-2,2-dimethyl-4-[1-(2-naphthylmethyl-1,2,5,6-tetrahydropyrid-4-yl]-2H-chromene 7-n-Amyl-2,2-dimethyl-4-(4-pyridyl)-2H-chromen-5-ol (6.36 g) was dissolved in benzene (50 ml) and sodium hydride (0.88 g of a 60% dispersion in mineral oil) was added portionwise. The mixture was stirred for 15 minutes and a solution of iodomethane (3.14 g) in benzene (20 ml) was added dropwise. At the end of the addition, the mixture was treated under reflux for 1.5 hours. After cooling, the mixture was poured into water (130 ml) and extracted with ether. The combined organic extracts were dried over sodium sulphate and evaporated in vacuo. The crude residual oil was purified via column chromatography on silica gel using diethyl-ether/60°–80° petroleum ether as eluent to yield 7-n-amyl-5-methoxy-2,2-dimethyl-4-(4-pyridyl)-2H-chromene as a yellow oil (4.15 g).

This 4-(4-pyridyl)-2H-chromene (4.15 g), 2-bromomethyl naphthalene (2.87 g) and acetone (50 ml) were heated together under reflux for 13 hours. Dry diethyl-ether was then added to the cooled solution and the resulting precipitate of 4-(7-n-amyl-5-methoxy-2,2-dimethyl-2H-chromen-4-yl)-1-(2-naphthylmethyl)-pyridinium bromide (4.55 g, m.p. 93°–95°) was filtered and dried.

This quaternary salt (4.55 g) was dissolved in ethanol (120 ml) and water (40 ml) and excess sodium borohydride was added portionwise to the stirred solution at ambient temperature. Work-up as described in Example 1 yielded the tetrahydropyridine (2.44 g) as a gum (purified via column chromatography on silica gel using diethyl-ether/60°–80° petroleum-ether as eluent).

EXAMPLE 8

Pharmacology

Metacorticoid hypertension was induced in rats by the method of Green et al. [Amer. J. Physiol., 170, 94 (1952)]. All compounds were suspended in methyl cellulose and administered orally to groups of at least three metacorticoid hypertensive rats at a dose of 100 mg/kg. The blood pressure was measured indirectly in conscious restrained rats by the method of Friedman et al. ]Proc. Soc. Exper. Biol. Med., 70, 670 (1949)]. The following results were obtained for compounds of the formula:

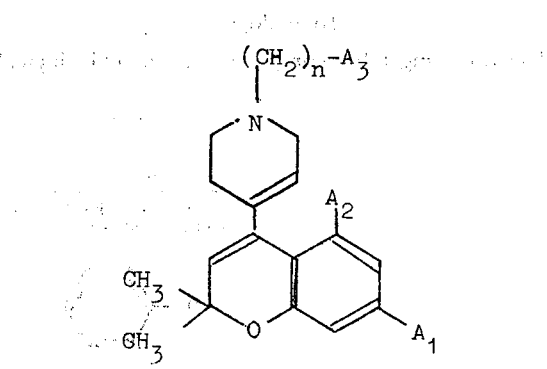

| $A_1$ | $A_2$ | $A_3$ | n | Percentage change in systolic blood pressure at hrs post-dose | | |
|---|---|---|---|---|---|---|
| | | | | 4 hrs | 6 hrs | 24 hrs |
| Control (receiving 1% w/v methyl cellulose) | | | | −3 | — | −5 |
| —(CH$_2$)$_4$CH$_3$ | —OH | 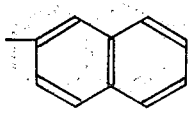 | 1 | −20 | — | −12 |

-continued

| $A_1$ | $A_2$ | $A_3$ | n | \multicolumn{3}{c}{Percentage change in systolic blood pressure at hrs post-dose} |
|---|---|---|---|---|---|---|
| | | | | 4 hrs | 6 hrs | 24 hrs |
| $-(CH_2)_4CH_3$ | $-OH$ | 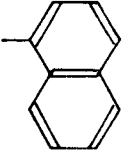 | 1 | No result obtained | -- | -17 |
| $-(CH_2)_4CH_3$ | $-OH$ | 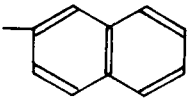 | 2 | -19 | -15 | -8 |
| $-CH(CH_2)_3CH_3$ / $CH_3$ | $-OH$ | 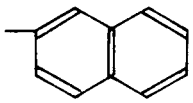 | 1 | -15 | -10 | -20 |
| $-CH(CH_2)_3CH_3$ / $CH_3$ | $-OH$ | 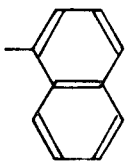 | 1 | -10 | -13 | -15 |
| $-(CH_2)_4CH_3$ | $-O.COCH_3$ | 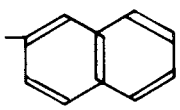 | 1 | -11 | -10 | -22 |
| $-(CH_2)_4CH_3$ | $-O.CO(CH_2)_3N(C_2H_5)(C_2H_5)$ .2HCl | 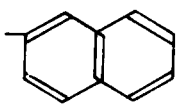 | 1 | -7 | -7 | -9 |
| $-(CH_2)_4CH_3$ | $-OCH_3$ | 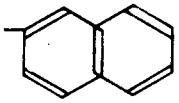 | 1 | -21 | -28 | -5 |

Toxicology

The following table compares certain toxicological and were administered daily at 60 mg/kg orally to groups of eight normotensive rats for 10 days.

| R | General depression | Weight gain (g) | Blood urea nitrogen (mg/100 ml) | pH of urine (after loading with NH₄Cl) |
|---|---|---|---|---|
| Control (receiving 1% w/v methyl cellulose) | 0 | 43.4 | 21.0 | 5.8 |
| 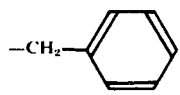 | ++ | 24.5 | 23.0 | 6.3 |
| 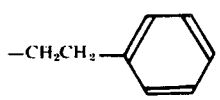 | ++ | 20.8 | 24.8 | 6.8 |
| 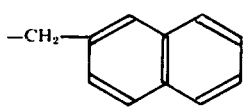 | 0 | 41.0 | 17.3 | 5.8 | parameters of one of the compounds of the present invention with those of two of the compounds disclosed in British Pat. No. 1,360,009. These compounds have the formula:

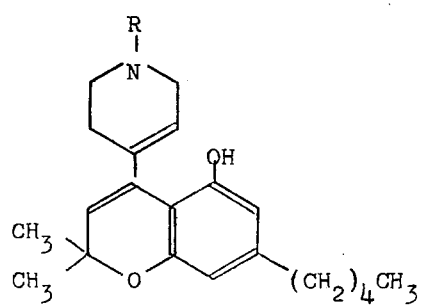

What is claimed is:
1. A compound of the formula

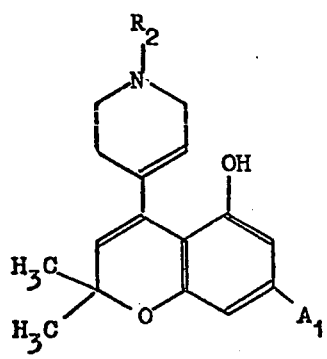

wherein R is alkyl of 4–8 carbon atoms, $R_2$ is naphthylmethyl, an ester or ether thereof wherein the phenolic hydroxyl moiety is substituted by $R_3$ or $COR_3$ wherein $R_3$ is methyl, ethyl, propyl, dimethylamino, diethylamino, dimethylaminopropyl, diethylaminopropyl, or N-piperidylethyl, or a pharmaceutically acceptable non-toxic salt thereof.

2. A compound of the formula

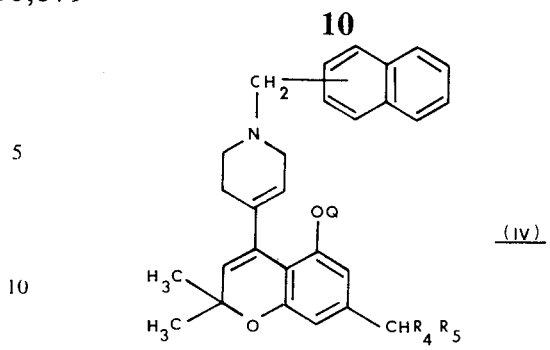

or a pharmaceutically acceptable non-toxic salt thereof wherein Q is hydrogen, methyl or acetyl; $R_4$ is hydrogen or methyl and $R_5$ is n-propyl, n-butyl or n-pentyl.

3. A compound according to claim 2 wherein $R_5$ is n-butyl.

4. A compound according to claim 2 wherein $R_4$ is hydrogen.

5. A compound according to claim 2 wherein $R_4$ is hydrogen.

6. The compound of claim 1 which is 7-n-amyl-2,2-dimethyl-4-[1-(1-naphthylmethyl)-1,2,5,6-tetrahydropyrid-4-yl]-2H-chromen-5-ol.

7. The compound of claim 1 which is 7-n-amyl-2,2-dimethyl-4-[1-(2-naphthylmethyl)-1,2,5,6-tetrahydropyrid-4-yl]-2H-chromen-5-ol.

8. A compound according to claim 2 wherein Q is hydrogen.

9. The compound according to claim 1 which is 7-(2-hexyl)-2,2-dimethyl-4-[1-(2-naphthylmethyl)-1,2,5,6-tetrahydropyrid-4-yl]-2H-chromen-5-ol.

10. The compound according to claim 1 which is 7-(2-hexyl)-2,2-dimethyl-4-[1-(1-naphthylmethyl)-1,2,5,6-tetrahydropyrid-4-yl]-2H-chromen-5-ol.

11. The compound according to claim 1 which is 5-acetoxy-7-n-amyl-2,2-dimethyl-4-[1-(2-naphthylmethyl)-1,2,5,6-tetrahydropyrid-4-yl]-2H-chromene.

12. The compound according to claim 1 which is 4-diethylaminobutoxy-7-(n-amyl)-4-[1-(2-naphthylmethyl)-1,2,5,6-tetrahydropyrid-4-yl]-2,2-dimethyl-2H-chromen-5-yl dihydrochloride.

13. The compound according to claim 1 which is 7-(n-amyl)-5-methoxy-2,2-dimethyl-4-[1-(2-naphthylmethyl)-1,2,5,6-tetrahydropyrid-4-yl]-2H-chromene.

* * * * *